(12) United States Patent
Lee et al.

(10) Patent No.: US 12,138,001 B2
(45) Date of Patent: Nov. 12, 2024

(54) PATIENT CONSOLE 5-DEGREE OF FREEDOM POSITIONING SYSTEMS

(71) Applicant: EndoQuest Robotics, Inc., Houston, TX (US)

(72) Inventors: Jeihan Lee, Houston, TX (US); Jaesun Lee, Seongnam (KR); Jiwon Choi, Houston, TX (US); Dongsuk Shin, Houston, TX (US)

(73) Assignee: EndoQuest Robotics, Inc., Houston, TX (US)

( * ) Notice: Subject to any disclaimer, the term of this patent is extended or adjusted under 35 U.S.C. 154(b) by 57 days.

(21) Appl. No.: 18/122,007

(22) Filed: Mar. 15, 2023

(65) Prior Publication Data

US 2023/0285098 A1 Sep. 14, 2023

Related U.S. Application Data

(63) Continuation of application No. PCT/US2022/051220, filed on Nov. 29, 2022.

(Continued)

(51) Int. Cl.
*A61B 34/37* (2016.01)
*A61B 34/00* (2016.01)
*A61B 34/30* (2016.01)

(52) U.S. Cl.
CPC .............. *A61B 34/37* (2016.02); *A61B 34/25* (2016.02); *A61B 34/74* (2016.02); *A61B 2034/303* (2016.02)

(58) Field of Classification Search
CPC ... A61B 2034/303; A61B 34/25; A61B 34/30; A61B 34/37; A61B 34/74
See application file for complete search history.

(56) References Cited

U.S. PATENT DOCUMENTS

| 5,792,135 A | 8/1998 | Madhani et al. |
| 5,797,900 A | 8/1998 | Madhani et al. |

(Continued)

FOREIGN PATENT DOCUMENTS

| CN | 105310775 A | 2/2016 |
| CN | 108309370 A | 7/2018 |

(Continued)

OTHER PUBLICATIONS

"Plenary 1: Colubris MX"—YouTube Video link address https://www.youtube.com/watch?v=in_IuQiAZg8 dated Aug. 20, 2020.

(Continued)

*Primary Examiner* — Scott Luan
(74) *Attorney, Agent, or Firm* — Locke Lord LLP; Scott D. Wofsy; Michael J. Pollack

(57) ABSTRACT

A patient console for a robotic surgical system can include a base, a vertical lift attached to a top of the base and configured to provide up and down motion in a vertical axis, a yaw rotation device attached to the top of the vertical lift and configured to provide a yaw rotation about the vertical axis, a pitch rotation device attached to the top of the yaw rotation device and configured to provide a pitch rotation about a pitch axis orthogonal to the vertical axis, a translation device attached to the top of the pitch rotation device and configured to provide sliding translation along a translation axis, and a roll rotation device attached to the translation device to roll relative to the translation device about a roll axis to provide a roll to an instrument controller assembly. An angle of the translation axis and the roll axis relative to horizontal can be a function of the pitch rotation provided by the pitch rotation device. A direction of the translation axis and the roll axis can be a function of the yaw rotation provided by the yaw rotation device.

20 Claims, 10 Drawing Sheets

Related U.S. Application Data

(60) Provisional application No. 63/284,499, filed on Nov. 30, 2021.

(56) References Cited

U.S. PATENT DOCUMENTS

| | | |
|---|---|---|
| 5,976,122 A | 11/1999 | Madhani et al. |
| 6,063,095 A | 5/2000 | Wang et al. |
| 6,132,368 A | 10/2000 | Cooper |
| 6,244,809 B1 | 6/2001 | Wang et al. |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,346,072 B1 | 2/2002 | Cooper |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,451,027 B1 | 9/2002 | Cooper et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,522,906 B1 | 2/2003 | Salisbury, Jr. et al. |
| 6,565,554 B1 | 5/2003 | Niemeyer |
| 6,587,750 B2 | 7/2003 | Gerbi et al. |
| 6,645,196 B1 | 11/2003 | Nixon et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,746,443 B1 | 6/2004 | Morley et al. |
| 6,766,204 B2 | 7/2004 | Niemeyer et al. |
| 6,783,524 B2 | 8/2004 | Anderson et al. |
| 6,785,593 B2 | 8/2004 | Wang et al. |
| 6,799,088 B2 | 9/2004 | Wang et al. |
| 6,817,972 B2 | 11/2004 | Snow |
| 6,817,974 B2 | 11/2004 | Cooper et al. |
| 6,836,703 B2 | 12/2004 | Wang et al. |
| 6,837,846 B2 | 1/2005 | Jaffe et al. |
| 6,840,938 B1 | 1/2005 | Morley et al. |
| 6,852,107 B2 | 2/2005 | Wang et al. |
| 6,866,671 B2 | 3/2005 | Tierney et al. |
| 6,871,117 B2 | 3/2005 | Wang et al. |
| 6,892,112 B2 | 5/2005 | Wang et al. |
| 6,905,491 B1 | 6/2005 | Wang et al. |
| 6,951,535 B2 | 10/2005 | Ghodoussi et al. |
| 6,991,627 B2 | 1/2006 | Madhani et al. |
| 6,994,703 B2 | 2/2006 | Wang et al. |
| 7,025,064 B2 | 4/2006 | Wang et al. |
| 7,027,892 B2 | 4/2006 | Wang et al. |
| 7,048,745 B2 | 5/2006 | Tierney et al. |
| 7,066,926 B2 | 6/2006 | Wallace et al. |
| 7,074,179 B2 | 7/2006 | Wang et al. |
| 7,083,571 B2 | 8/2006 | Wang et al. |
| 7,087,049 B2 | 8/2006 | Nowlin et al. |
| 7,090,637 B2 | 8/2006 | Danitz et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,204,844 B2 | 4/2007 | Jensen et al. |
| 7,276,065 B2 | 10/2007 | Morley et al. |
| 7,320,700 B2 | 1/2008 | Cooper et al. |
| 7,331,967 B2 | 2/2008 | Lee et al. |
| 7,333,642 B2 | 2/2008 | Green |
| 7,357,774 B2 | 4/2008 | Cooper |
| 7,398,707 B2 | 7/2008 | Morley et al. |
| 7,524,320 B2 | 4/2009 | Tierney et al. |
| 7,574,250 B2 | 8/2009 | Niemeyer |
| 7,608,083 B2 | 10/2009 | Lee et al. |
| 7,615,066 B2 | 11/2009 | Danitz et al. |
| 7,691,098 B2 | 4/2010 | Wallace et al. |
| 7,744,608 B2 | 6/2010 | Lee et al. |
| 7,756,036 B2 | 7/2010 | Druke et al. |
| 7,757,028 B2 | 7/2010 | Druke et al. |
| 7,763,015 B2 | 7/2010 | Cooper et al. |
| 7,780,651 B2 | 8/2010 | Madhani et al. |
| 7,837,674 B2 | 11/2010 | Cooper |
| 7,854,738 B2 | 12/2010 | Lee et al. |
| 7,865,266 B2 | 1/2011 | Moll et al. |
| 7,955,322 B2 | 6/2011 | Devengenzo et al. |
| 8,052,636 B2 | 11/2011 | Moll et al. |
| 8,054,752 B2 | 11/2011 | Druke et al. |
| 8,068,649 B2 | 11/2011 | Green |
| 8,075,474 B2 | 12/2011 | Honda et al. |
| 8,100,133 B2 | 1/2012 | Mintz et al. |
| 8,120,301 B2 | 2/2012 | Goldberg et al. |
| 8,123,740 B2 | 2/2012 | Madhani et al. |
| 8,147,503 B2 | 4/2012 | Zhao et al. |
| 8,169,468 B2 | 5/2012 | Scott et al. |
| 8,182,415 B2 | 5/2012 | Larkin et al. |
| 8,190,238 B2 | 5/2012 | Moll et al. |
| 8,228,368 B2 | 7/2012 | Zhao et al. |
| 8,323,297 B2 | 12/2012 | Hinman et al. |
| 8,335,590 B2 | 12/2012 | Costa et al. |
| 8,337,521 B2 | 12/2012 | Cooper et al. |
| 8,343,045 B2 | 1/2013 | Swinehart et al. |
| 8,343,141 B2 | 1/2013 | Madhani et al. |
| 8,365,633 B2 | 2/2013 | Simaan et al. |
| 8,375,808 B2 | 2/2013 | Blumenkranz et al. |
| 8,398,541 B2 | 3/2013 | DiMaio et al. |
| 8,437,629 B2 | 5/2013 | McDowall |
| 8,469,947 B2 | 6/2013 | Devengenzo et al. |
| 8,475,366 B2 | 7/2013 | Boulais et al. |
| 8,506,555 B2 | 8/2013 | Ruiz Morales |
| 8,594,841 B2 | 11/2013 | Zhao et al. |
| 8,597,280 B2 | 12/2013 | Cooper et al. |
| 8,600,551 B2 | 12/2013 | Itkowitz et al. |
| 8,617,102 B2 | 12/2013 | Moll et al. |
| 8,644,988 B2 | 2/2014 | Prisco et al. |
| 8,679,099 B2 | 3/2014 | Cooper et al. |
| 8,690,908 B2 | 4/2014 | Cooper et al. |
| 8,709,000 B2 | 4/2014 | Madhani et al. |
| 8,740,885 B2 | 6/2014 | Larkin et al. |
| 8,784,435 B2 | 7/2014 | Cooper et al. |
| 8,786,241 B2 | 7/2014 | Nowlin et al. |
| 8,790,243 B2 | 7/2014 | Cooper et al. |
| 8,801,661 B2 | 8/2014 | Moll et al. |
| 8,810,631 B2 | 8/2014 | Scott et al. |
| 8,816,628 B2 | 8/2014 | Nowlin et al. |
| 8,821,480 B2 | 9/2014 | Burbank |
| 8,831,782 B2 | 9/2014 | Itkowitz |
| 8,838,270 B2 | 9/2014 | Druke et al. |
| 8,852,208 B2 | 10/2014 | Gomez et al. |
| 8,887,595 B2 | 11/2014 | Williams |
| 8,888,690 B2 | 11/2014 | Swinehart et al. |
| 8,888,764 B2 | 11/2014 | Devengenzo et al. |
| 8,903,549 B2 | 12/2014 | Itkowitz et al. |
| 8,918,207 B2 | 12/2014 | Prisco |
| 8,944,070 B2 | 2/2015 | Guthart et al. |
| 8,945,095 B2 | 2/2015 | Blumenkranz et al. |
| 9,011,318 B2 | 4/2015 | Choset et al. |
| 9,050,120 B2 | 6/2015 | Swarup et al. |
| 9,060,678 B2 | 6/2015 | Larkin et al. |
| 9,089,354 B2 | 7/2015 | Simaan et al. |
| 9,095,362 B2 | 8/2015 | Dachs, II et al. |
| 9,138,284 B2 | 9/2015 | Krom et al. |
| 9,144,456 B2 | 9/2015 | Rosa et al. |
| 9,186,221 B2 | 11/2015 | Burbank |
| 9,254,090 B2 | 2/2016 | Watson et al. |
| 9,259,274 B2 | 2/2016 | Prisco |
| 9,259,276 B2 | 2/2016 | Mintz et al. |
| 9,301,807 B2 | 4/2016 | Duval |
| 9,308,937 B2 | 4/2016 | Griffiths et al. |
| 9,339,341 B2 | 5/2016 | Cooper |
| 9,358,074 B2 | 6/2016 | Schena et al. |
| 9,456,839 B2 | 10/2016 | Cooper |
| 9,486,288 B2 | 11/2016 | Devengenzo et al. |
| 9,498,242 B2 | 11/2016 | Crews et al. |
| 9,504,517 B2 | 11/2016 | Rosa et al. |
| 9,510,915 B2 | 12/2016 | Madhani et al. |
| 9,565,990 B2 | 2/2017 | Lee et al. |
| 9,687,310 B2 | 6/2017 | Nowlin et al. |

(56) References Cited

U.S. PATENT DOCUMENTS

| | | |
|---|---|---|
| 9,717,486 B2 | 8/2017 | Cooper et al. |
| 9,757,149 B2 | 9/2017 | Cooper et al. |
| 9,757,203 B2 | 9/2017 | Hourtash et al. |
| 9,775,678 B2 | 10/2017 | Lohmeier |
| 9,782,056 B2 | 10/2017 | McDowall |
| 9,782,225 B2 | 10/2017 | Lohmeier et al. |
| 9,795,446 B2 | 10/2017 | DiMaio et al. |
| 9,795,453 B2 | 10/2017 | Tierney et al. |
| 9,801,526 B2 | 10/2017 | Larkin et al. |
| 9,801,654 B2 | 10/2017 | Gomez et al. |
| 9,814,527 B2 | 11/2017 | Rogers et al. |
| 9,877,794 B2 | 1/2018 | Csiky |
| 9,901,402 B2 | 2/2018 | Itkowitz et al. |
| 9,918,659 B2 | 3/2018 | Chopra et al. |
| 9,949,620 B2 | 4/2018 | Duval et al. |
| 9,962,066 B2 | 5/2018 | Rogers et al. |
| 9,968,405 B2 | 5/2018 | Cooper et al. |
| 9,980,630 B2 | 5/2018 | Larkin et al. |
| 10,010,331 B2 | 7/2018 | Morash |
| 10,039,473 B2 | 8/2018 | Zhao et al. |
| 10,058,390 B2 | 8/2018 | Simaan et al. |
| 10,085,788 B2 | 10/2018 | Privitera et al. |
| 10,085,806 B2 | 10/2018 | Hagn et al. |
| 10,092,172 B2 | 10/2018 | Peh et al. |
| 10,105,128 B2 | 10/2018 | Cooper et al. |
| 10,117,715 B2 | 11/2018 | Lohmeier et al. |
| 10,159,536 B2 | 12/2018 | Kralicky et al. |
| 10,178,368 B2 | 1/2019 | Zhao et al. |
| 10,179,024 B2 | 1/2019 | Yeung |
| 10,179,413 B2 | 1/2019 | Rockrohr |
| 10,188,472 B2 | 1/2019 | Diolaiti et al. |
| 10,258,421 B2 | 4/2019 | Lohmeier et al. |
| 10,278,782 B2 | 5/2019 | Jarc et al. |
| 10,321,964 B2 | 6/2019 | Grover et al. |
| 10,327,856 B2 | 6/2019 | Kralicky et al. |
| 10,363,107 B2 | 7/2019 | Blumenkranz et al. |
| 10,365,295 B2 | 7/2019 | Blumenkranz et al. |
| 10,390,687 B2 | 8/2019 | Choi et al. |
| 10,390,895 B2 | 8/2019 | Henderson et al. |
| 10,391,635 B2 | 8/2019 | Berghofer et al. |
| 10,398,520 B2 | 9/2019 | Larkin et al. |
| 10,413,370 B2 | 9/2019 | Yates et al. |
| 10,448,813 B2 | 10/2019 | Cooper et al. |
| 10,456,166 B2 | 10/2019 | Cooper et al. |
| 10,507,068 B2 | 12/2019 | Kopp et al. |
| 10,512,481 B2 | 12/2019 | Cooper |
| 10,524,644 B2 | 1/2020 | Scott et al. |
| 10,524,868 B2 | 1/2020 | Cooper et al. |
| 10,531,929 B2 | 1/2020 | Widenhouse et al. |
| 10,602,958 B2 | 3/2020 | Silverstein et al. |
| 10,646,990 B2 | 5/2020 | Olds et al. |
| 10,660,713 B2 | 5/2020 | McCrea et al. |
| 10,682,193 B2 | 6/2020 | Choi et al. |
| 10,729,503 B2 | 8/2020 | Cameron |
| 10,736,702 B2 | 8/2020 | Harris et al. |
| 10,779,896 B2 | 9/2020 | Dachs, II et al. |
| 10,779,899 B2 | 9/2020 | Griffiths et al. |
| 10,786,329 B2 | 9/2020 | Schuh et al. |
| 10,820,953 B2 | 11/2020 | Kralicky et al. |
| 10,828,115 B2 | 11/2020 | Koenig et al. |
| 10,828,117 B2 | 11/2020 | Evans |
| 10,835,331 B2 | 11/2020 | Burbank |
| 10,835,335 B2 | 11/2020 | Perdue et al. |
| 10,856,946 B2 | 12/2020 | Solomon et al. |
| 10,864,051 B2 | 12/2020 | Simi et al. |
| 10,874,475 B2 | 12/2020 | Iceman |
| 10,881,422 B2 | 1/2021 | Kim et al. |
| 10,898,189 B2 | 1/2021 | McDonald, II |
| 10,898,281 B2 | 1/2021 | Cooper et al. |
| 10,905,505 B1 | 2/2021 | Barakat et al. |
| 10,918,449 B2 | 2/2021 | Solomon et al. |
| 10,939,970 B2 | 3/2021 | Laakso et al. |
| 10,959,607 B2 | 3/2021 | Rogers et al. |
| 11,037,464 B2 | 6/2021 | Ho et al. |
| 2002/0161281 A1 | 10/2002 | Jaffe et al. |
| 2003/0036748 A1 | 2/2003 | Cooper et al. |
| 2003/0083673 A1 | 5/2003 | Tierney et al. |
| 2003/0114962 A1 | 6/2003 | Niemeyer |
| 2003/0135203 A1 | 7/2003 | Wang et al. |
| 2004/0049205 A1 | 3/2004 | Lee et al. |
| 2004/0138700 A1 | 7/2004 | Cooper et al. |
| 2004/0162547 A1 | 8/2004 | Wallace et al. |
| 2004/0236316 A1 | 11/2004 | Danitz et al. |
| 2005/0043718 A1 | 2/2005 | Madhani et al. |
| 2005/0059960 A1 | 3/2005 | Simaan et al. |
| 2005/0149003 A1 | 7/2005 | Tierney et al. |
| 2005/0200324 A1 | 9/2005 | Guthart et al. |
| 2005/0204851 A1 | 9/2005 | Morley et al. |
| 2005/0216033 A1 | 9/2005 | Lee et al. |
| 2005/0251112 A1 | 11/2005 | Danitz et al. |
| 2006/0167440 A1 | 7/2006 | Cooper et al. |
| 2007/0043338 A1 | 2/2007 | Moll et al. |
| 2007/0137372 A1 | 6/2007 | Devengenzo et al. |
| 2007/0151390 A1 | 7/2007 | Blumenkranz et al. |
| 2007/0156119 A1 | 7/2007 | Wallace et al. |
| 2007/0156122 A1 | 7/2007 | Cooper |
| 2007/0197896 A1 | 8/2007 | Moll et al. |
| 2008/0065105 A1 | 3/2008 | Larkin et al. |
| 2008/0065107 A1 | 3/2008 | Larkin et al. |
| 2008/0065111 A1 | 3/2008 | Blumenkranz et al. |
| 2008/0071291 A1 | 3/2008 | Duval et al. |
| 2008/0077159 A1 | 3/2008 | Madhani et al. |
| 2008/0177282 A1 | 7/2008 | Lee et al. |
| 2008/0177284 A1 | 7/2008 | Lee et al. |
| 2008/0287963 A1 | 11/2008 | Rogers et al. |
| 2009/0023989 A1 | 1/2009 | Honda et al. |
| 2009/0171151 A1 | 7/2009 | Choset et al. |
| 2010/0011901 A1 | 1/2010 | Burbank |
| 2010/0048999 A1 | 2/2010 | Boulais et al. |
| 2010/0082041 A1 | 4/2010 | Prisco |
| 2010/0234831 A1 | 9/2010 | Hinman et al. |
| 2010/0274087 A1 | 10/2010 | Diolaiti et al. |
| 2010/0292708 A1 | 11/2010 | Madhani et al. |
| 2011/0118755 A1 | 5/2011 | Cooper et al. |
| 2011/0125166 A1 | 5/2011 | Cooper et al. |
| 2011/0144658 A1 | 6/2011 | Wenderow et al. |
| 2011/0152879 A1 | 6/2011 | Williams |
| 2011/0196419 A1 | 8/2011 | Cooper |
| 2011/0277580 A1 | 11/2011 | Cooper et al. |
| 2011/0282351 A1 | 11/2011 | Cooper et al. |
| 2011/0282359 A1 | 11/2011 | Duval |
| 2011/0282491 A1 | 11/2011 | Prisco et al. |
| 2011/0288561 A1 | 11/2011 | Devengenzo et al. |
| 2011/0313449 A1 | 12/2011 | Cooper |
| 2012/0150192 A1 | 6/2012 | Dachs, II et al. |
| 2012/0203271 A1 | 8/2012 | Larkin et al. |
| 2012/0209174 A1 | 8/2012 | Moll et al. |
| 2012/0221011 A1 | 8/2012 | Larkin et al. |
| 2012/0232339 A1 | 9/2012 | Csiky |
| 2013/0053868 A1 | 2/2013 | Cooper et al. |
| 2013/0079794 A9 | 3/2013 | Cooper et al. |
| 2013/0096540 A1 | 4/2013 | Cooper et al. |
| 2013/0110131 A1 | 5/2013 | Madhani et al. |
| 2013/0197539 A1 | 8/2013 | Simaan et al. |
| 2013/0197540 A1 | 8/2013 | Simaan et al. |
| 2013/0267950 A1 | 10/2013 | Rosa et al. |
| 2013/0267964 A1 | 10/2013 | Rogers et al. |
| 2013/0274761 A1 | 10/2013 | Devengenzo et al. |
| 2014/0081292 A1 | 3/2014 | Moll et al. |
| 2014/0194899 A1 | 7/2014 | Madhani et al. |
| 2014/0243852 A1 | 8/2014 | Cooper et al. |
| 2014/0257336 A1 | 9/2014 | Choi et al. |
| 2014/0277106 A1 | 9/2014 | Crews et al. |
| 2014/0296637 A1 | 10/2014 | Lee et al. |
| 2014/0296872 A1 | 10/2014 | Cooper et al. |
| 2015/0066002 A1 | 3/2015 | Cooper et al. |
| 2015/0100066 A1 | 4/2015 | Kostrzewski et al. |
| 2015/0150636 A1 | 6/2015 | Hagn et al. |
| 2015/0173726 A1 | 6/2015 | Lohmeier et al. |
| 2015/0173729 A1 | 6/2015 | Lohmeier et al. |
| 2015/0173731 A1 | 6/2015 | Lohmeier et al. |
| 2015/0173840 A1 | 6/2015 | Lohmeier |
| 2015/0238267 A1 | 8/2015 | Devengenzo et al. |
| 2015/0250546 A1 | 9/2015 | Larkin et al. |

(56) References Cited

U.S. PATENT DOCUMENTS

| | | |
|---|---|---|
| 2016/0015447 A1 | 1/2016 | Rosa et al. |
| 2016/0058512 A1 | 3/2016 | Gomez et al. |
| 2016/0066773 A1 | 3/2016 | Cooper et al. |
| 2016/0242860 A1 | 8/2016 | Diolaiti et al. |
| 2016/0256183 A1 | 9/2016 | Cooper |
| 2017/0014197 A1 | 1/2017 | McCrea et al. |
| 2017/0020615 A1 | 1/2017 | Koenig et al. |
| 2017/0071628 A1 | 3/2017 | Cooper et al. |
| 2017/0112505 A1 | 4/2017 | Morash |
| 2017/0156804 A1 | 6/2017 | Cooper et al. |
| 2017/0265923 A1 | 9/2017 | Privitera et al. |
| 2017/0273749 A1 | 9/2017 | Grover et al. |
| 2017/0274533 A1 | 9/2017 | Berghofer et al. |
| 2017/0281296 A1 | 10/2017 | Cooper et al. |
| 2017/0312043 A1 | 11/2017 | Ogawa et al. |
| 2017/0325879 A1 | 11/2017 | Yeung |
| 2017/0354318 A1 | 12/2017 | Rogers et al. |
| 2017/0367775 A1 | 12/2017 | Dachs, II et al. |
| 2017/0367777 A1 | 12/2017 | Kralicky et al. |
| 2018/0000318 A9 | 1/2018 | Rogers et al. |
| 2018/0000548 A1 | 1/2018 | Olds et al. |
| 2018/0014852 A1 | 1/2018 | Gomez et al. |
| 2018/0049820 A1 | 2/2018 | Widenhouse et al. |
| 2018/0049822 A1 | 2/2018 | Henderson et al. |
| 2018/0049827 A1 | 2/2018 | Harris et al. |
| 2018/0064498 A1 | 3/2018 | Kapadia et al. |
| 2018/0111273 A1 | 4/2018 | Linnell et al. |
| 2018/0132956 A1 | 5/2018 | Cameron |
| 2018/0168747 A1 | 6/2018 | Kopp et al. |
| 2018/0168752 A1 | 6/2018 | Scheib et al. |
| 2018/0193007 A1 | 7/2018 | Au et al. |
| 2018/0200894 A1 | 7/2018 | Rockrohr |
| 2018/0214176 A1 | 8/2018 | Solomon et al. |
| 2018/0221096 A1 | 8/2018 | Yates et al. |
| 2018/0242824 A1 | 8/2018 | Larkin et al. |
| 2018/0256270 A1 | 9/2018 | Cooper et al. |
| 2018/0271607 A1 | 9/2018 | Kralicky et al. |
| 2018/0271616 A1 | 9/2018 | Schuh et al. |
| 2018/0286287 A1 | 10/2018 | Razzaque |
| 2018/0296299 A1 | 10/2018 | Iceman |
| 2018/0317915 A1 | 11/2018 | McDonald, II |
| 2018/0318023 A1 | 11/2018 | Griffiths et al. |
| 2018/0353204 A1 | 12/2018 | Solomon et al. |
| 2018/0370045 A1 | 12/2018 | Kan |
| 2019/0039241 A1 | 2/2019 | Langenfeld et al. |
| 2019/0117247 A1 | 4/2019 | Kim et al. |
| 2019/0125467 A1 | 5/2019 | Evans |
| 2019/0216551 A1 | 7/2019 | Burbank |
| 2019/0269472 A1 | 9/2019 | Kralicky et al. |
| 2019/0274769 A1 | 9/2019 | Perdue et al. |
| 2019/0314645 A1 | 10/2019 | Ciresianu et al. |
| 2019/0328472 A1 | 10/2019 | Tojo et al. |
| 2019/0380801 A1 | 12/2019 | Savall et al. |
| 2020/0038123 A1 | 2/2020 | Graetzel et al. |
| 2020/0069389 A1 | 3/2020 | Morrissette et al. |
| 2020/0078097 A1 | 3/2020 | Gregerson et al. |
| 2020/0107898 A1 | 4/2020 | Kim et al. |
| 2020/0146763 A1 | 5/2020 | Schena et al. |
| 2020/0179067 A1 | 6/2020 | Ross et al. |
| 2020/0205917 A1 | 7/2020 | Peine et al. |
| 2020/0214774 A1 | 7/2020 | Yoshida et al. |
| 2020/0297444 A1 | 9/2020 | Camarillo et al. |
| 2020/0315645 A1 | 10/2020 | Kim et al. |
| 2020/0330173 A1 | 10/2020 | Kapadia et al. |
| 2020/0367979 A1 | 11/2020 | Laakso et al. |
| 2020/0397456 A1 | 12/2020 | Kim et al. |
| 2020/0397457 A1 | 12/2020 | Kim et al. |
| 2021/0045819 A1 | 2/2021 | Castillo et al. |
| 2021/0077195 A1 | 3/2021 | Saeidi et al. |
| 2021/0241542 A1 | 8/2021 | Shmayahu et al. |
| 2021/0259794 A1 | 8/2021 | Kato et al. |
| 2021/0267702 A1 | 9/2021 | Kim et al. |
| 2021/0275266 A1 | 9/2021 | Kim et al. |
| 2021/0322045 A1 | 10/2021 | Kim et al. |
| 2021/0322046 A1 | 10/2021 | Kim et al. |
| 2021/0338052 A1 | 11/2021 | Ouyang et al. |
| 2022/0354524 A1 | 11/2022 | Kim et al. |
| 2023/0210618 A1 | 7/2023 | Kim et al. |
| 2023/0210621 A1 | 7/2023 | Noh et al. |
| 2023/0248419 A1 | 8/2023 | Cho et al. |
| 2023/0248450 A1 | 8/2023 | Ravi et al. |
| 2023/0248457 A1 | 8/2023 | Lee et al. |
| 2023/0255702 A1 | 8/2023 | Park et al. |
| 2023/0285090 A1 | 9/2023 | Lee et al. |
| 2023/0285099 A1 | 9/2023 | Lee et al. |
| 2023/0355221 A1 | 11/2023 | Shin et al. |
| 2023/0363842 A1 | 11/2023 | Choi et al. |
| 2023/0363847 A1 | 11/2023 | Lee et al. |
| 2024/0058079 A1 | 2/2024 | Kim et al. |

FOREIGN PATENT DOCUMENTS

| | | |
|---|---|---|
| CN | 109674647 A | 4/2019 |
| CN | 213606867 U | 7/2021 |
| EP | 2968048 B1 | 6/2018 |
| EP | 3175813 B1 | 1/2020 |
| JP | 2019530517 A | 10/2019 |
| JP | 2020104843 A | 7/2020 |
| JP | 2021513442 A | 5/2021 |
| KR | 20110032444 A | 3/2011 |
| KR | 101943440 B1 | 1/2019 |
| WO | 2012/035492 A1 | 3/2012 |
| WO | 2016/109886 A1 | 7/2016 |
| WO | 2019055681 A1 | 3/2019 |
| WO | 2020243285 A1 | 12/2020 |
| WO | 2021026231 A1 | 2/2021 |
| WO | 2021071540 A1 | 4/2021 |
| WO | 2021161162 A1 | 8/2021 |
| WO | 2021161184 A1 | 8/2021 |

OTHER PUBLICATIONS

International Search Report and Written Opinion, of the Korean Intellectual Property Office, as ISA, mailed Apr. 6, 2023, in corresponding International Patent Application PCT/US2022/051217.

International Search Report and Written Opinion, of the Korean Intellectual Property Office, as ISA, mailed Apr. 6, 2023, in corresponding International Patent Application PCT/US2022/051220.

International Search Report and Written Opinion, of the Korean Intellectual Property Office, as ISA, mailed Apr. 7, 2023, in corresponding International Patent Application PCT/US2022/051225.

International Search Report and Written Opinion, of the Korean Intellectual Property Office, as ISA, mailed Apr. 6, 2023, in corresponding International Patent Application PCT/US2022/051237.

International Search Report and Written Opinion, of the Korean Intellectual Property Office, as ISA, mailed Apr. 6, 2023, in corresponding International Patent Application PCT/US2022/051246.

International Search Report and Written Opinion, of the Korean Intellectual Property Office, as ISA, mailed Apr. 6, 2023, in corresponding International Patent Application PCT/US2022/051255.

International Search Report and Written Opinion, of the Korean Intellectual Property Office, as ISA, mailed Apr. 6, 2023, in corresponding International Patent Application PCT/US2022/051259.

International Search Report and Written Opinion, of the Korean Intellectual Property Office, as ISA, mailed Apr. 6, 2023, in corresponding International Patent Application PCT/US2022/051261.

International Search Report and Written Opinion, of the Korean Intellectual Property Office, as ISA, mailed Apr. 14, 2023, in corresponding International Patent Application PCT/US2022/051265.

International Search Report and Written Opinion, of the Korean Intellectual Property Office, as ISA, mailed Apr. 6, 2023, in corresponding International Patent Application PCT/US2022/051262.

Office Action mailed Jun. 16, 2023, issued for Taiwanese Patent Application No. 111145621 and English translation of the Search Report.

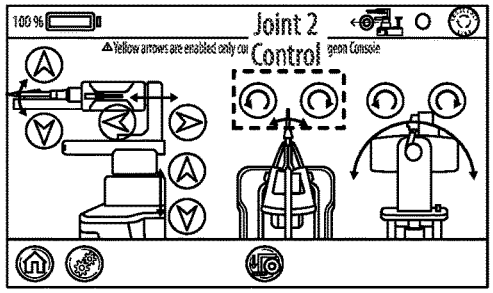
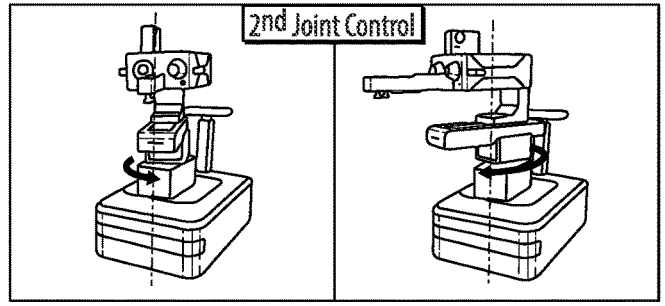
Fig. 9A
Fig. 9B
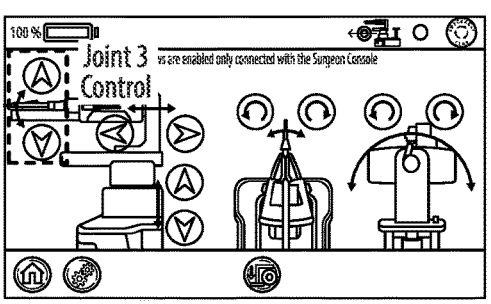
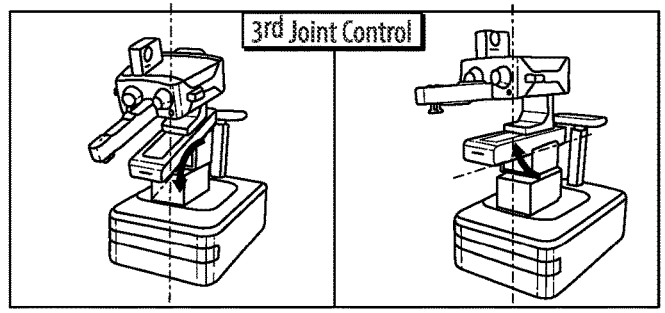
Fig. 10A
Fig. 10B
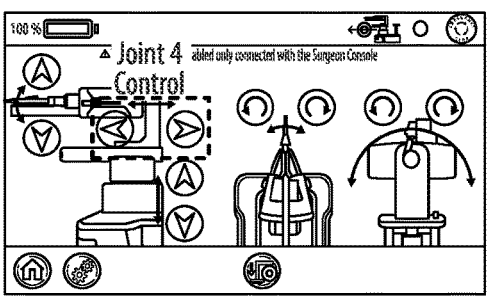
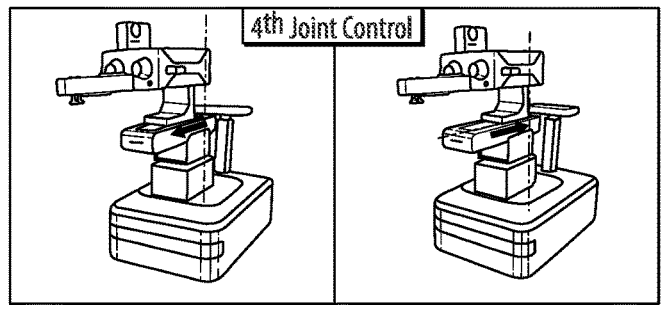
Fig. 11A
Fig. 11B

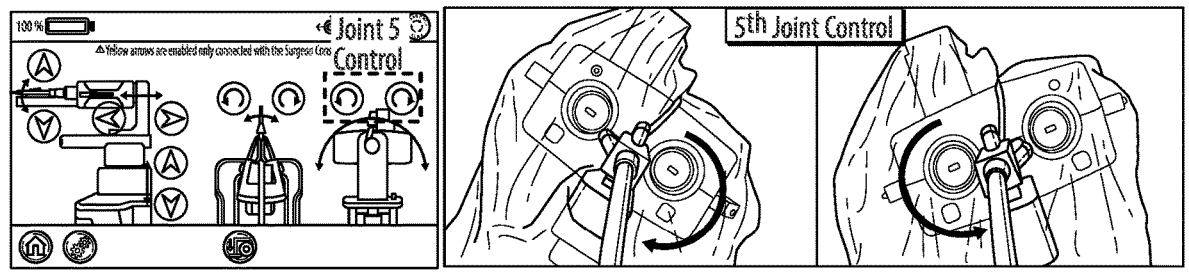
Fig. 12A  Fig. 12B
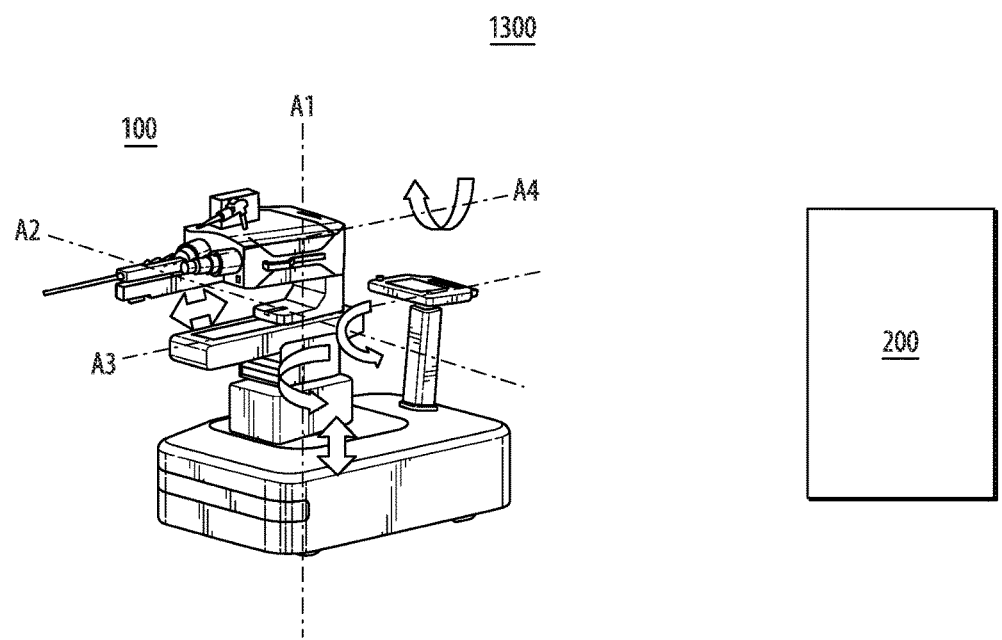
Fig. 13

PATENT CONSOLE 5-DEGREE OF FREEDOM POSITIONING SYSTEMS

CROSS-REFERENCE TO RELATED APPLICATIONS

This application is a continuation of International Patent Application No. PCT/US2022/051220 filed Nov. 29, 2022, which claims priority to and the benefit of U.S. Provisional Application No. 63/284,499, filed Nov. 30, 2021, the entire contents of which are herein incorporated by reference in their entirety.

FIELD

This disclosure relates to robotic surgical systems, e.g., for minimally invasive surgery including, but not limited to, endoluminal and single-site surgery.

BACKGROUND

Minimally invasive surgery such as endoluminal and single-site robotic surgery offer significant advantages versus traditional robotic surgery. For example, in endoluminal robotic surgery, no incision need be made to access difficult to access locations within a patient's natural lumen. This dramatically reduces and/or eliminates recovery time and improves procedural safety. A single-site system reduces incisions to a minimum single-site, which reduces an otherwise larger number of incisions to provide access for certain procedures.

Certain endoluminal and single-site robotic surgical systems have been proposed. Examples of such systems and related components can be found in U.S. Pat. No. 10,881,422, as well as U.S. Patent Application Nos. US20210322046, US20210322045, US20190117247, US20210275266, US20210267702, US20200107898, US20200397457, US202000397456, US20200315645, and US201962914226, all of the above being incorporated by reference herein in their entirety.

Conventional surgical robotics and systems have generally been considered satisfactory for their intended purpose. However, there is still a need in the art for improved robotic surgical systems, devices, methods, controls, and components, especially those configured for endoluminal and single-site surgery. The present disclosure provides improvements in such areas, for example.

SUMMARY

In accordance with at least one aspect of this disclosure, a patient console for a robotic surgical system can include a base, a vertical lift attached to a top of the base and configured to provide up and down motion in a vertical axis, a yaw rotation device attached to the top of the vertical lift and configured to provide a yaw rotation about the vertical axis, a pitch rotation device attached to the top of the yaw rotation device and configured to provide a pitch rotation about a pitch axis orthogonal to the vertical axis, a translation device attached to the top of the pitch rotation device and configured to provide sliding translation along a translation axis, and a roll rotation device attached to the translation device to roll relative to the translation device about a roll axis to provide a roll to an instrument controller assembly. An angle of the translation axis and the roll axis relative to horizontal can be a function of the pitch rotation provided by the pitch rotation device. A direction of the translation axis and the roll axis can be a function of the yaw rotation provided by the yaw rotation device.

The patient console can include an instrument controller assembly connected to the roll rotation device, the instrument controller assembly including one or more instrument controllers for controlling a medical device for performing a surgical operation, wherein the vertical lift, the yaw rotation device, the pitch rotation device, the translation device, and the roll rotation device provide 5-degrees of freedom to the instrument controller assembly. In certain embodiments, the base can be configured to move relative to a floor to provide an additional degree of freedom of motion.

The patient console can be configured to allow for positioning of a medical device for a transanal procedure, a transoral procedure, or a transvaginal procedure. Any other suitable procedure is contemplated herein.

The patient console can include a user input device attached to the base and configured to control each of the vertical lift, the yaw rotation device, the pitch rotation device, the translation device, and the roll rotation device. The user input device can include a display having a graphical user interface (GUI) for controlling each of the vertical lift, the yaw rotation device, the pitch rotation device, the translation device, and the roll rotation device. The GUI can be configured to indicate an orientation and position of the instrument controller assembly from one or more angles. The GUI can be configured to have any suitable digital buttons, inputs, indicators, images, text, and/or other content.

In accordance with at least one aspect of this disclosure, a robotic surgical system, can include a patient console. The patient console can be any patient console disclosed herein, e.g., as described above.

In accordance with at least one aspect of this disclosure, a method for performing a robotic medical procedure can include using a vertical lift attached to a top of a base of a patient console to provide up and down motion in a vertical axis, using a yaw rotation device attached to the top of the vertical lift to provide a yaw rotation about the vertical axis, using a pitch rotation device attached to the top of the yaw rotation device and configured to provide a pitch rotation about a pitch axis orthogonal to the vertical axis, using a translation device attached to the top of the pitch rotation device and configured to provide sliding translation along a translation axis, and using a roll rotation device attached to the translation device to roll relative to the translation device about a roll axis to provide a roll to an instrument controller assembly. An angle of the translation axis and the roll axis relative to horizontal can be a function of the pitch rotation provided by the pitch rotation device. A direction of the translation axis and the roll axis can be a function of the yaw rotation provided by the yaw rotation device.

The method can include using an instrument controller assembly having one or more instrument controllers connected to the roll rotation device for controlling a medical device for performing a surgical operation, and using the vertical lift, the yaw rotation device, the pitch rotation device, the translation device, and the roll rotation device provide 5-degrees of freedom to the instrument controller assembly. The method can include moving the base of the patient console relative to a floor to provide an additional degree of freedom of motion. The method can include positioning a medical device for a transanal procedure, a transoral procedure, or a transvaginal procedure.

The method can include controlling each of the vertical lift, the yaw rotation device, the pitch rotation device, the translation device, and the roll rotation device with a user input device. The method can include using a graphical user interface (GUI) to control each of the vertical lift, the yaw rotation device, the pitch rotation device, the translation device, and the roll rotation device. The method can include any other suitable method(s) and/or portion(s) thereof.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIGS. 9A and 9B illustrate a control the second joint, e.g., a yaw rotation device as shown;

FIGS. 10A and 10B illustrate a control the third joint, e.g., a pitch rotation device as shown;

FIGS. 11A and 11B illustrate a control the fourth joint, e.g., a translation device as shown;

FIGS. 12A and 12B illustrate a control the fifth joint, e.g., a roll rotation device; and FIG. 13 illustrates an embodiment of a robotic surgical system in accordance with this disclosure.

DETAILED DESCRIPTION

Figure 1:
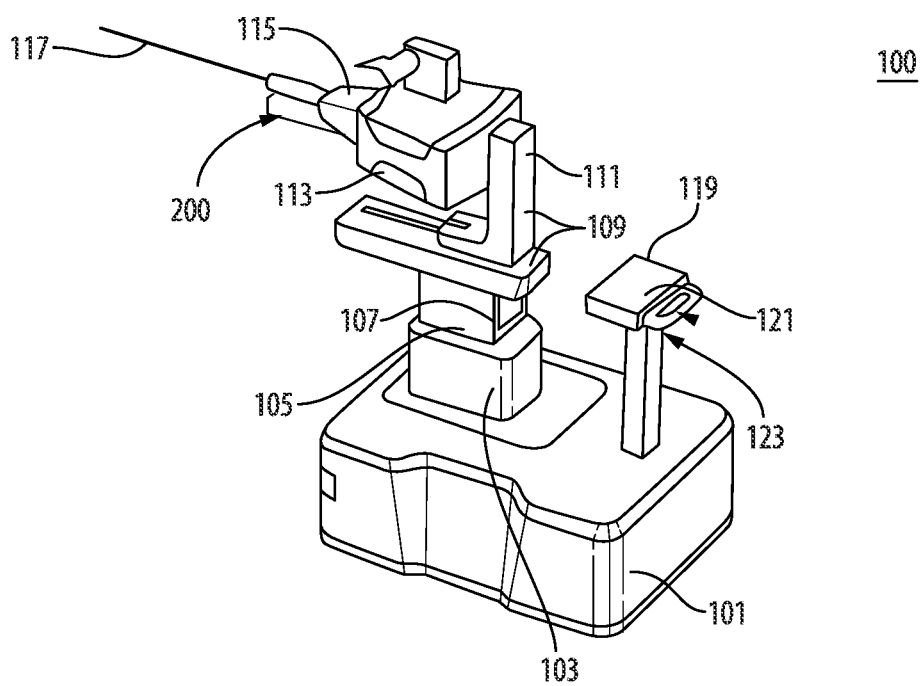
FIG. 1 is a perspective view of an embodiment of a patient console in accordance with this disclosure.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1 and is designated generally by reference character 100. Other embodiments and/or aspects of this disclosure are shown in FIGS. 2-13.

Referring to FIGS. 1-6 a patient console 100 (e.g., a cart) for a robotic surgical system can include a base 101 and a positioning arm 102. The positioning arm 102 can include a vertical lift 103 (e.g., joint J1) attached to a top of the base 101 and configured to provide up and down motion in a vertical axis A1. The patient console 100 can include a yaw rotation device 105 (e.g., joint J2) attached to the top of the vertical lift 103 and configured to provide a yaw rotation about the vertical axis A1. The patient console 100 can include a pitch rotation device 107 (e.g., joint J3) attached to the top of the yaw rotation device 105 to provide a pitch rotation about a pitch axis A2 orthogonal to the vertical axis A1. The patient console 100 can include a translation device 109 (e.g., joint J4) attached to the top of the pitch rotation device 107 and configured to provide sliding translation along a translation axis A3. The patient console 100 can include a roll rotation device 111 (e.g., joint J5) attached to the translation device 109 to roll relative to the translation device 109 about a roll axis A4 to provide a roll to an instrument controller assembly 113.

An angle of the translation axis A3 and the roll axis A4 relative to horizontal can be a function of the pitch rotation provided by the pitch rotation device 107. A direction of the translation axis A3 and the roll axis A4 can be a function of the yaw rotation provided by the yaw rotation device 105.

The console 100 can include an instrument controller assembly 113 connected to the roll rotation device 111, the instrument controller assembly 113 including one or more instrument controllers 115 for controlling a medical device (not shown) for performing a surgical operation. The vertical lift 103, the yaw rotation device 105, the pitch rotation device 107, the translation device 109, and the roll rotation device 111 can provide 5-degrees of freedom to the instrument controller assembly 113 (and thus the overtube 117 mounted thereon), for example. In certain embodiments, the base 101 can be configured to move relative to a floor to provide an additional degree of freedom of motion.

The patient console 100 can be configured to allow for positioning of a medical device for a transanal procedure, a transoral procedure, or a transvaginal procedure. Any other suitable procedure is contemplated herein.

Figure 7:
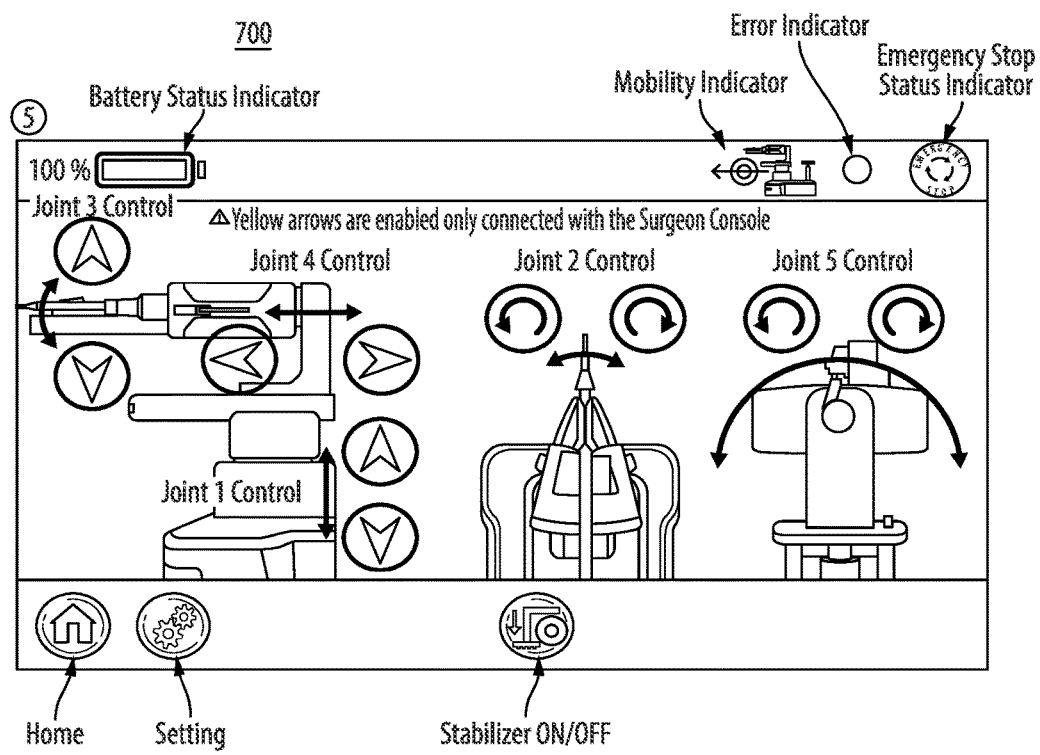
FIG. 7 shows an embodiment of a graphical user interface (GUI) for an embodiment of a user input device of the patient console.

The system 100 can include a user input device 119 attached to the base 101 and configured to control each of the vertical lift 103, the yaw rotation device 105, the pitch rotation device 107, the translation device 109, and the roll rotation device 111. Referring additionally to FIG. 7, the user input device 119 can include a display 121 (e.g., a touchscreen) having a graphical user interface (GUI) 700 for controlling each of the vertical lift 103, the yaw rotation device 105, the pitch rotation device 107, the translation device 109, and the roll rotation device 111. As shown, the GUI 700 can be configured to indicate an orientation and position of the instrument controller assembly 113 from one or more angles. The GUI 700 can be configured to have any suitable digital buttons, inputs, indicators, images, text, and/or other content (e.g., arrow buttons indicating the direction of rotation as shown and/or any other indicators and/or control buttons.

In certain embodiments, one or more of the vertical lift 103, the yaw rotation device 105, the pitch rotation device 107, the translation device 109, and the roll rotation device 111 can be controlled by a remote surgeon console in addition to the user input device 119, for example. In certain embodiments, the user input device 119 can control all of the vertical lift 103, the yaw rotation device 105, the pitch rotation device 107, the translation device 109, and the roll rotation device 111, and a remote surgeon console can control the translation device 109 and the roll rotation device 111 only.

Figure 2:
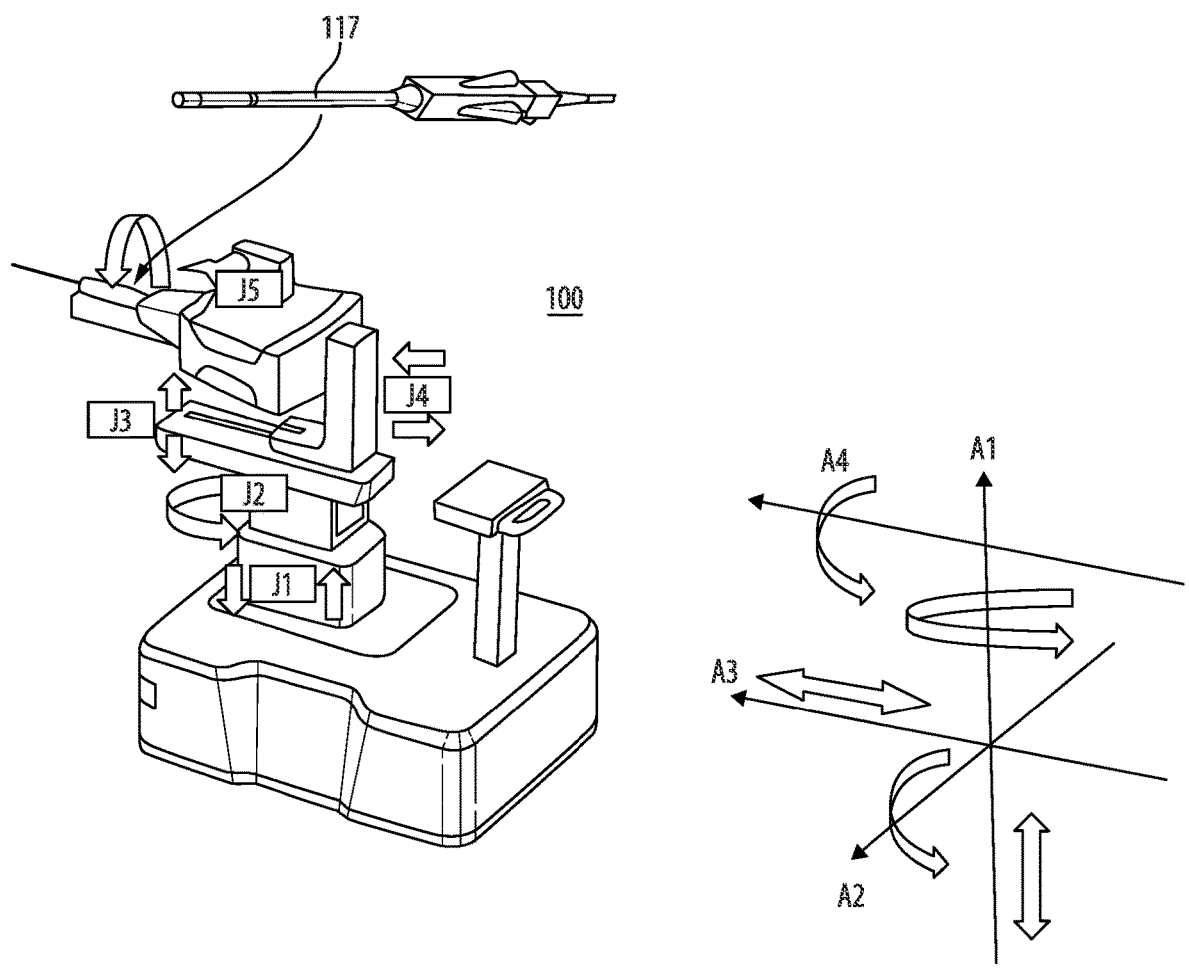
FIG. 2 is a schematic view of the embodiment of FIG. 1, showing five degrees of freedom at five joints.
Figure 2A:
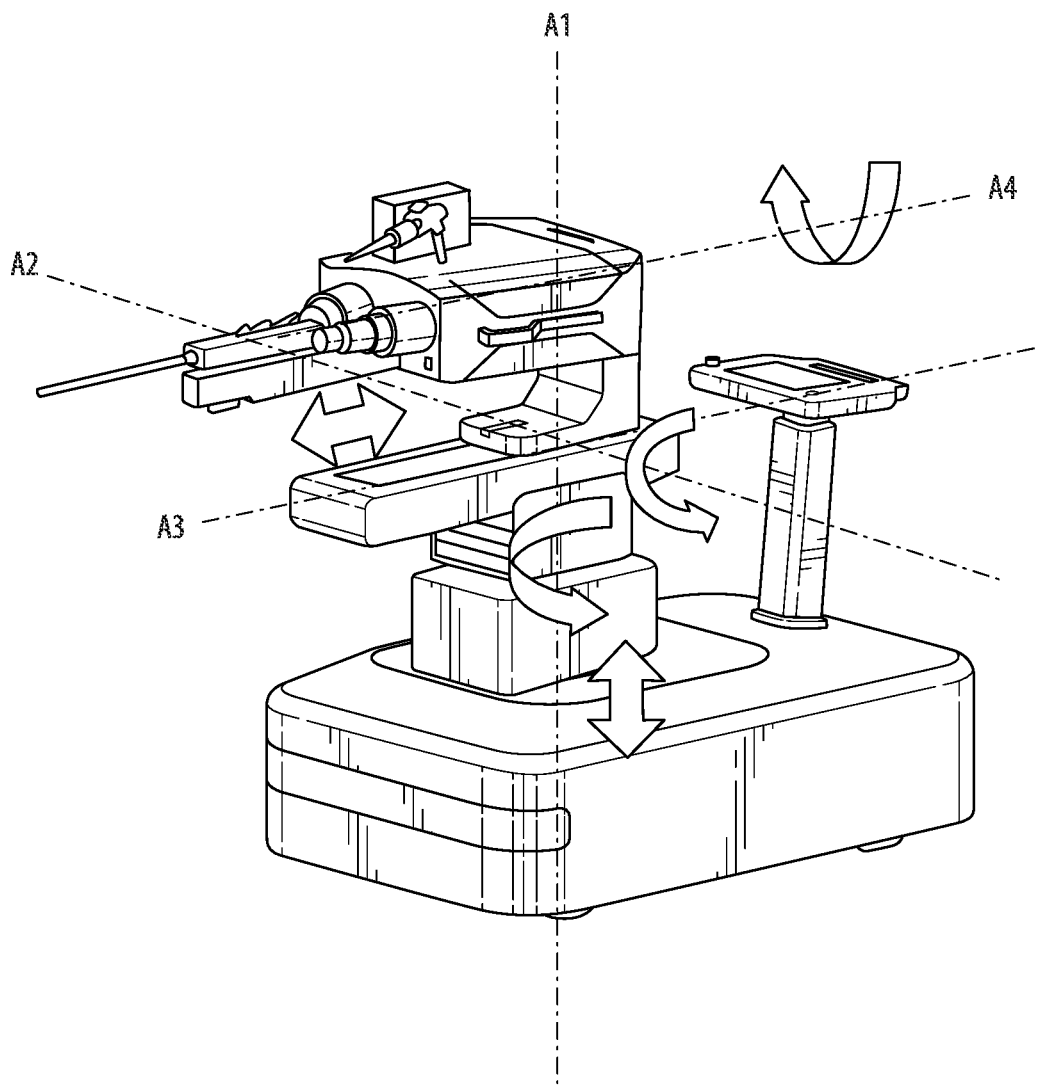
FIG. 2A is a schematic view of the embodiment as shown in FIG. 2, illustrating axes of motion (e.g., A1, A2, A3, and A4)
Figure 3:
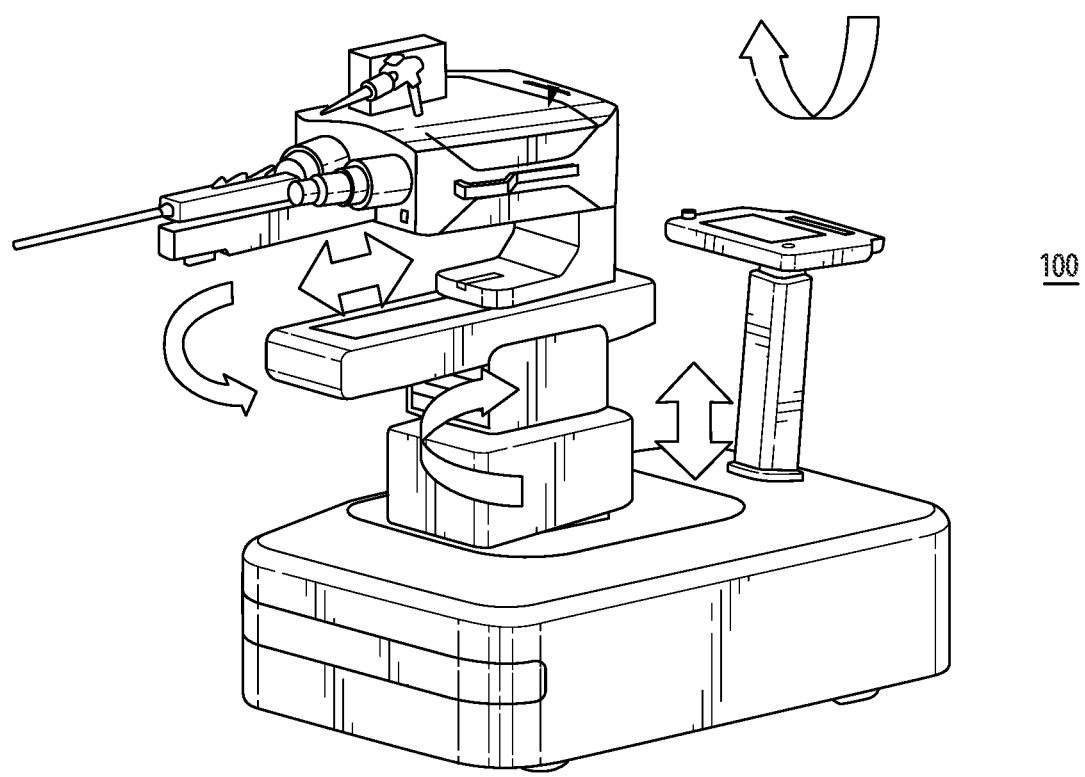
FIG. 3 is another view of the embodiment of FIG. 2, showing the five degrees of freedom.

FIG. 1 is a perspective view of an embodiment of a patient console in accordance with this disclosure. FIG. 2 is a schematic view of the embodiment of FIG. 1, showing five degrees of freedom at five joints (e.g., J1, J2, J3, J4, J5). FIG.

Figure 4:
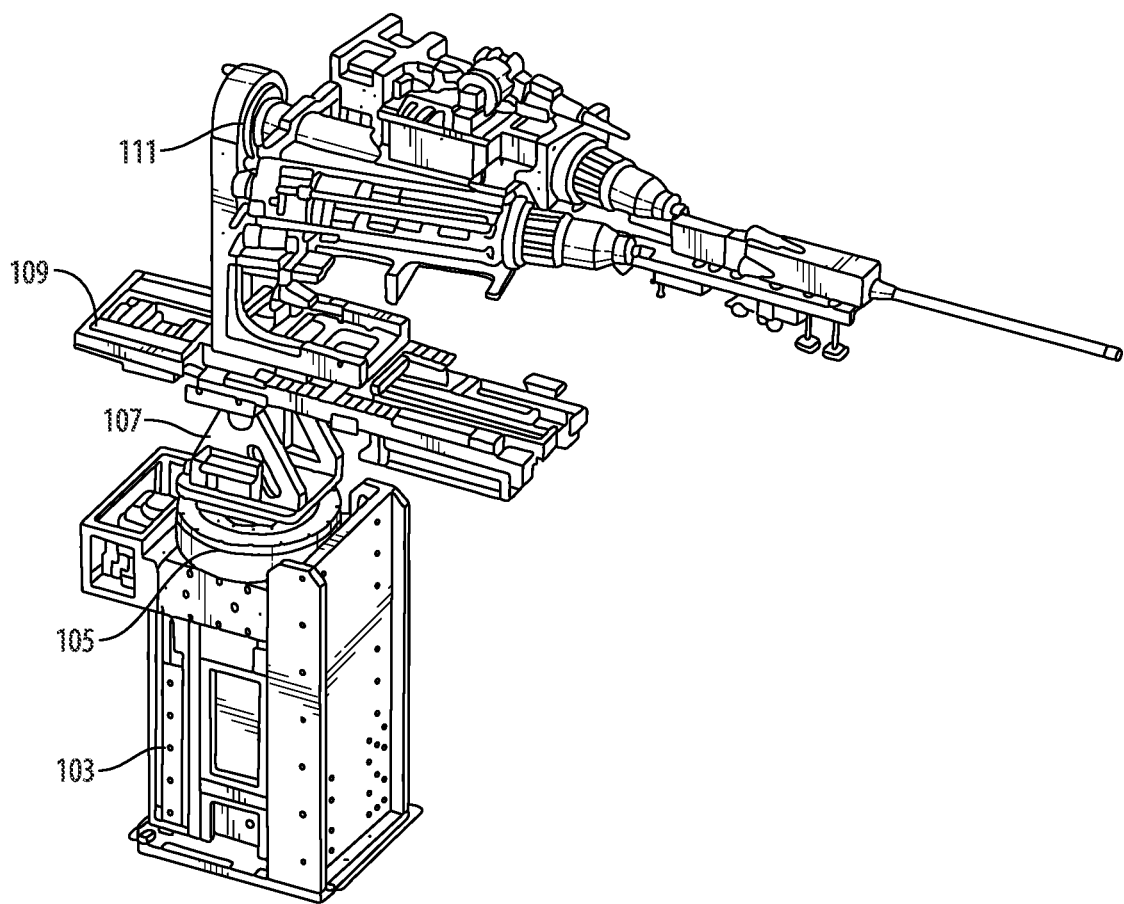
FIG. 4 is an elevation view of the embodiment of FIG. 1, showing in a storage position.
Figure 5:
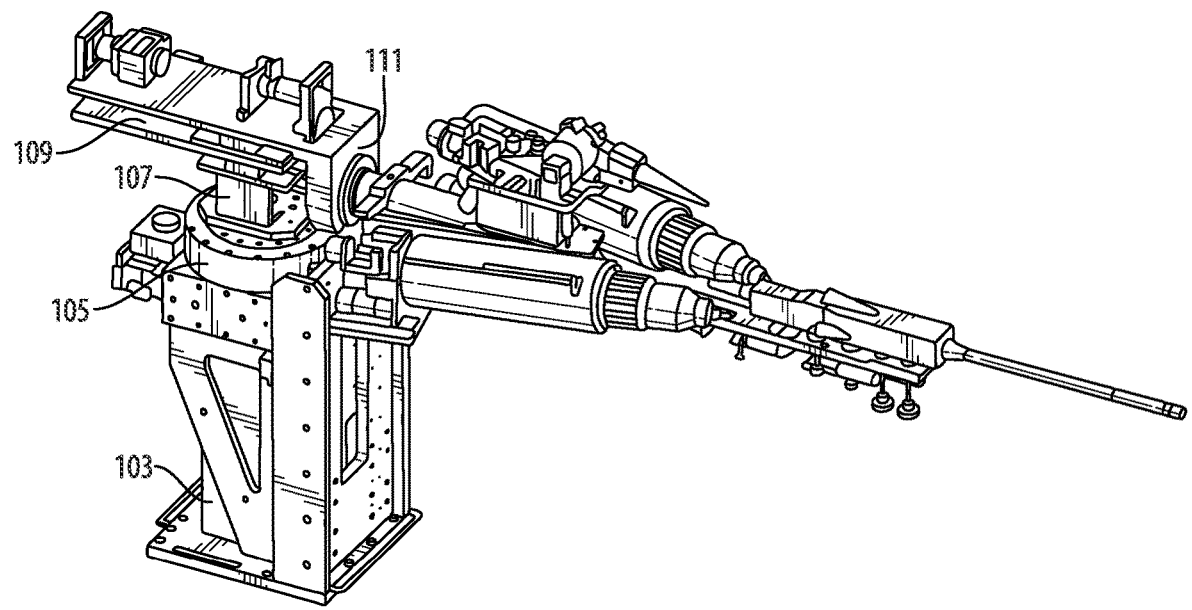
FIG. 5 is a perspective view of the embodiment of FIG. 1, showing the positioning components and with the base and outer housing removed.
Figure 6:
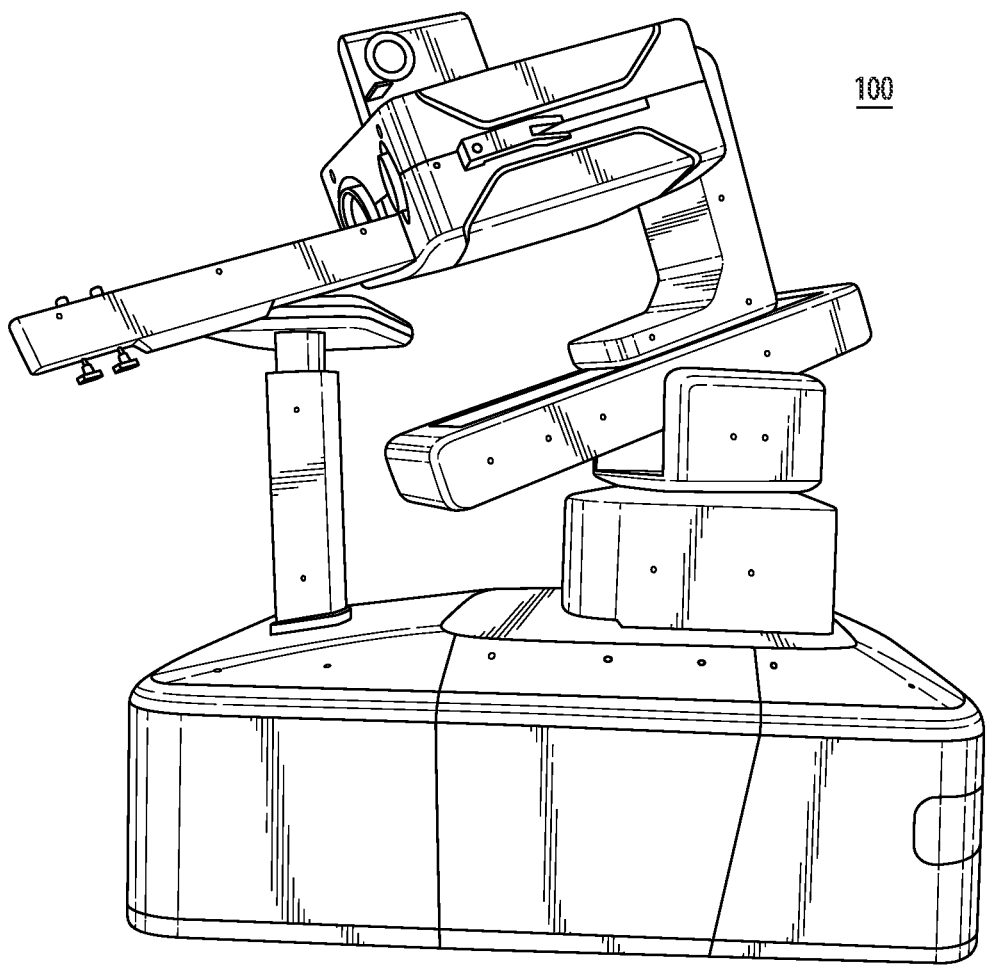
FIG. 6 is a perspective view of another embodiment of the positioning components of a patient console and with the base and outer housing removed.
Figure 8A:
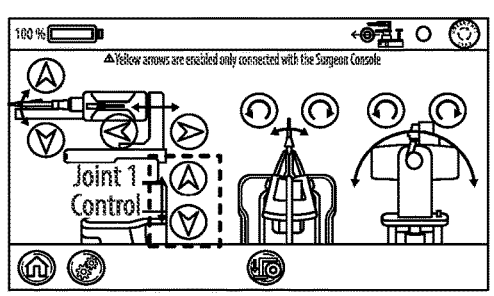
FIGS. 8A and 8B illustrate a control the first joint, e.g., a vertical lift as shown.
Figure 8B:
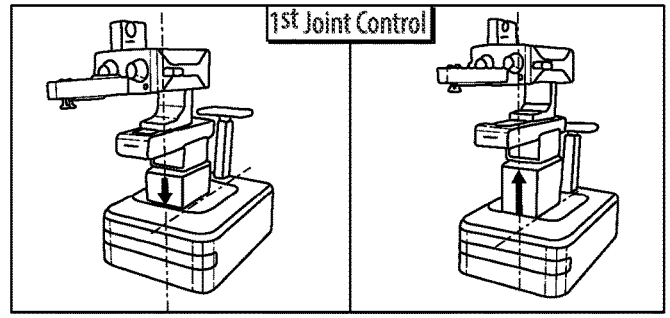

3 is another view of the embodiment of FIG. 2, showing the five degrees of freedom. FIG. 4 is an elevation view of the embodiment of FIG. 1, showing in a storage position. FIG. 5 is a perspective view of the embodiment of FIG. 1, showing the positioning components and with the base and outer housing removed. FIG. 6 is a perspective view of another embodiment of the positioning components of a patient console and with the base and outer housing removed. FIG. 7 shows an embodiment of a graphical user interface (GUI) for an embodiment of a user input device of the patient console. FIGS. 8A and 8B illustrate a control the first joint (e.g., J1 as shown in FIG. 2), e.g., a vertical lift as shown. FIGS. 9A and 9B illustrate a control the second joint (e.g., J2 as shown in FIG. 2), e.g., a yaw rotation device as shown. FIGS. 10A and 10B illustrate a control the third joint (e.g., J3 as shown in FIG. 2), e.g., a pitch rotation device as shown. FIGS. 11A and 11B illustrate a control the fourth joint (e.g., J4 as shown in FIG. 2), e.g., a translation device as shown. FIGS. 12A and 12B illustrate a control the fifth joint (e.g., J5 as shown in FIG. 2), e.g., a roll rotation device.

Embodiments can be used for robotic surgical systems, for example. Any suitable uses and/or embodiments for use are contemplated herein.

Embodiments include five degree of freedom positioning patient console 100 (e.g., a patient cart). Embodiments can include an advantageous order of stacking of the degrees of freedom.

Embodiments can provide movements for the position of the overtube 117 attached to the overtube arm 200. Embodiments can include five joints and each joint provides specific motion. In certain embodiments, joint 1 (e.g., J1 as shown in FIG. 2) can provide up/down motion within 0-400 mm. In certain embodiments, joint 2 (e.g., J2 as shown in FIG. 2) can provide rotation motion within −90-+150 degrees. In certain embodiments, joint 3 (e.g., J3 as shown in FIG. 2) can provide tilting motion within 0-35 degrees downwards. In certain embodiments, joint 4 (e.g., J4 as shown in FIG. 2) can provide translation motion within 0-400 mm. In certain embodiments, joint 5 (e.g., J5 as shown in FIG. 2) can provide rolling motion within −170-+170 degrees.

In certain embodiments, all of the joints can be controlled by a nurse using the touchscreen on the patient console 100. Joint 4 and Joint 5 can be controlled by a surgeon by using the hand control devices and overtube pedal on the surgeon console (not shown).

Certain embodiments can include an interface (e.g. user input device 119) that has a touchscreen (e.g. the display 121), a base cart handle 123, and a stabilizer (not shown). Certain embodiments can allow control of the mobility of the patient console 100 system with drive control switches and the direction of force applied on the base cart handle 123. Certain embodiments can allow control via the base cart handle 123 is activated only when the drive control switches are pressed down halfway and held. Certain embodiments can be immobilized by activating the stabilizers via a touchscreen to prevent unwanted movement during surgery.

Embodiments of a user input device 119 can be used to control the positioning arm 102 and patient console 100. Embodiments of a user input device can indicate the status of the patient console 100. Embodiments of a user input device 119 can provide a setting menu for the base cart and its touchscreen. Embodiments of a user input device 119 can display buttons to control movements of the positioning arm 102.

Embodiments of a touchscreen GUI 700 can include a loading user interface that displays immediately when the power is on and initializes the patient console 100 and touchscreen. The GUI can include a home screen that provides access menu buttons to the Pose Setting, Patient Cart, and Diagnosis, for example. Embodiments of a GUI 700 can include a Patient Cart Setting Screen that provides detailed settings of the patient console 100 to adjust values related to mobility. The GUI 700 can include a Setting Screen that provides a setting menu to adjust the brightness of the touch screen. The GUI 700 can include a pose setting screen that provides touch buttons to adjust the pose setting of each joint of the positioning arm 102. In FIG. 7, various modes of exemplary indicators are provided in the GUI 700. Embodiments of a GUI can include a mobility indicator that shows whether the patient console 100 can be moved or not. Embodiments can include an error indicator that shows normal or abnormal status of the system with two colors of green and orange. If the error is occurred, orange color can be showing.

An emergency stop indicator can show activation of the emergency stop. When the emergency stop is activated, the icon can be changed to orange and red colors. Embodiments can include a home button that can provides function to return to the home screen. Embodiments can include a setting button that provides a function to activate a setting menu. Embodiments can include a stabilizer on/off button that provides a function to activate/deactivate the stabilizer of the patient console 100.

In certain embodiments, a user can move the positioning arm 102 to the required target region by using the positioning arm 102 touchscreen controls. A user can insert the overtube 117 into the patient, and then move the positioning arm 102 to align with the overtube 117. A user can then connect the overtube 117 to the overtube arm 200 and tighten the knobs.

The user can control the positioning arm 102 using the touchscreen controls provided on the patient console 100. The user can push the buttons provided on the touchscreen to move each joint of the positioning arm 102. The positioning arm 102 can provide five degrees of freedom of motion. A user can press and hold the button shown on the touchscreen to move the joint in the specified direction. The user can release the touchscreen button to stop moving the positioning arm 102. Table 1 shows an embodiment of motions provided by each joint J1-J5.

TABLE 1

| Joint | Motion Direction | Motion Direction |
| --- | --- | --- |
| J1 | Up | Down |
| J2 | Right | Left |
| J3 | Head Up | Head Down |
| J4 | Backward | Forward |
| J5 | Counterclockwise | Clockwise |

In certain embodiments, a surgeon can control the Joints 4 (e.g., J4) and 5 (e.g., J5) of the positioning arm 102 using hand control device along with an overtube pedal on a surgeon console. Any suitable other control scheme is contemplated herein.

In accordance with at least one aspect of this disclosure, referring to FIG. 13, a robotic surgical system 1300 can include a patient console 100. The patient console 100 can be any patient console disclosed herein, e.g., as described above. The robotic surgical system 1300 can include a surgeon console 200 configured to allow a surgeon to remotely operate one or more controllers connected to the patient console 100 (e.g., wirelessly or via a wired connection) to perform robotic surgery or other suitable medical procedure. Any suitable surgeon console 200 and/or control inputs are contemplated herein. In certain embodiments, the surgeon console 200 can be configured to allow control of one or more of the vertical lift 103, the yaw rotation device 105, the pitch rotation device 107, the translation device 109, and the roll rotation device 111 for positioning the medical instrument attached to the patient console 100 in situ. For example, the roll rotation device 111 can be configured to be operated by one or more hand controls of the surgeon console 200 to allow rotation of the overtube 117 (which contains one or more medical instruments and/or camera) about axis A4 to rotate the distal end of the medical device(s), camera, and/or overtube 117 in situ.

In accordance with at least one aspect of this disclosure, a method for performing a robotic medical procedure can include using a vertical lift 103 attached to a top of a base 101 of a patient console to provide up and down motion in a vertical axis A1, using a yaw rotation device 105 attached to the top of the vertical lift 103 to provide a yaw rotation about the vertical axis A1, using a pitch rotation device 107 attached to the top of the yaw rotation device 105 and configured to provide a pitch rotation about a pitch axis A2 orthogonal to the vertical axis A1, using a translation device 109 attached to the top of the pitch rotation device 107 and configured to provide sliding translation along a translation axis A3, and using a roll rotation device 111 attached to the translation device 109 to roll relative to the translation device 109 about a roll axis A4 to provide a roll to an instrument controller assembly 113. An angle of the translation axis A3 and the roll axis A4 relative to horizontal can be a function of the pitch rotation provided by the pitch rotation device 107 (about axis A2). A direction of the translation axis A3 and the roll axis A4 can be a function of the yaw rotation about the vertical axis A1 provided by the yaw rotation device 105.

The method can include using an instrument controller assembly 113 having one or more instrument controllers 115 connected to the roll rotation device 111 for controlling a medical device for performing a surgical operation, and using the vertical lift 103, the yaw rotation device 105, the pitch rotation device 107, the translation device 109, and the roll rotation device 111 provide 5-degrees of freedom to the instrument controller assembly 113. The method can include moving the base 101 of the patient console 100 relative to a floor (on which the patient console 100 is standing) to provide an additional degree of freedom of motion. The method can include positioning a medical device for a transanal procedure, a transoral procedure, or a transvaginal procedure.

The method can include controlling each of the vertical lift 103, the yaw rotation device 105, the pitch rotation device 107, the translation device 109, and the roll rotation device 111 with a user input device. The method can include using a graphical user interface (GUI) to control each of the vertical lift 103, the yaw rotation device 105, the pitch rotation device 107, the translation device 109, and the roll rotation device 111. The method can include any other suitable method(s) and/or portion(s) thereof.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A patient console for a robotic surgical system, comprising:
   a base; and
   a vertical lift attached to a top of the base and configured to provide up and down motion in a vertical axis;
   a yaw rotation device attached to the top of the vertical lift and configured to provide a yaw rotation about the vertical axis;
   a pitch rotation device attached to the top of the yaw rotation device and configured to provide a pitch rotation about a pitch axis orthogonal to the vertical axis;
   a translation device attached to the top of the pitch rotation device and configured to provide sliding translation along a translation axis; and
   a roll rotation device attached to the translation device to roll relative to the translation device about a roll axis to provide a roll to an instrument controller assembly, wherein an angle of the translation axis and the roll axis relative to horizontal is a function of the pitch rotation provided by the pitch rotation device, wherein a direction of the translation axis and the roll axis is a function of the yaw rotation provided by the yaw rotation device.

2. The patient console of claim 1, further comprising an instrument controller assembly connected to the roll rotation device, the instrument controller assembly including one or more instrument controllers for controlling a medical device for performing a surgical operation, wherein the vertical lift, the yaw rotation device, the pitch rotation device, the translation device, and the roll rotation device provide 5-degrees of freedom to the instrument controller assembly.

3. The patient console of claim 2, wherein the base is configured to move relative to a floor to provide an additional degree of freedom of motion.

4. The patient console of claim 3, wherein the patient console is configured to allow for positioning of a medical device for a transanal procedure, a transoral procedure, or a transvaginal procedure.

5. The patient console of claim 1, further comprising a user input device attached to the base and configured to control each of the vertical lift, the yaw rotation device, the pitch rotation device, the translation device, and the roll rotation device.

6. The patient console of claim 5, wherein the user input device includes a display having a graphical user interface (GUI) for controlling each of the vertical lift, the yaw rotation device, the pitch rotation device, the translation device, and the roll rotation device.

7. The patent console of claim 6, wherein the GUI is configured to indicate an orientation and position of the instrument controller assembly from one or more angles.

8. A robotic surgical system, comprising:
a patient console for a robotic surgical system, comprising:
a base; and
a vertical lift attached to a top of the base and configured to provide up and down motion in a vertical axis;
a yaw rotation device attached to the top of the vertical lift and configured to provide a yaw rotation about the vertical axis;
a pitch rotation device attached to the top of the yaw rotation device and configured to provide a pitch rotation about a pitch axis orthogonal to the vertical axis;
a translation device attached to the top of the pitch rotation device and configured to provide sliding translation along a translation axis; and
a roll rotation device attached to the translation device to roll relative to the translation device about a roll axis to provide a roll to an instrument controller assembly, wherein an angle of the translation axis and the roll axis relative to horizontal is a function of the pitch rotation provided by the pitch rotation device, wherein a direction of the translation axis and the roll axis is a function of the yaw rotation provided by the yaw rotation device.

9. The robotic surgical system of claim 8, wherein the patient console further includes an instrument controller assembly connected to the roll rotation device, the instrument controller assembly including one or more instrument controllers for controlling a medical device for performing a surgical operation, wherein the vertical lift, the yaw rotation device, the pitch rotation device, the translation device, and the roll rotation device provide 5-degrees of freedom to the instrument controller assembly.

10. The robotic surgical system of claim 9, wherein the base is configured to move relative to a floor to provide an additional degree of freedom of motion.

11. The robotic surgical system of claim 10, wherein the patient console is configured to allow for positioning of a medical device for a transanal procedure, a transoral procedure, or a transvaginal procedure.

12. The robotic surgical system of claim 8, wherein the patient console further includes a user input device attached to the base and configured to control each of the vertical lift, the yaw rotation device, the pitch rotation device, the translation device, and the roll rotation device.

13. The robotic surgical system of claim 12, wherein the user input device includes a display having a graphical user interface (GUI) for controlling each of the vertical lift, the yaw rotation device, the pitch rotation device, the translation device, and the roll rotation device.

14. The robotic surgical system of claim 13, wherein the GUI is configured to indicate an orientation and position of the instrument controller assembly from one or more angles.

15. The method of claim 12, further comprising using a graphical user interface (GUI) to control each of the vertical lift, the yaw rotation device, the pitch rotation device, the translation device, and the roll rotation device.

16. The method of claim 8, further comprising controlling each of the vertical lift, the yaw rotation device, the pitch rotation device, the translation device, and the roll rotation device with a user input device.

17. A method for performing a robotic medical procedure, comprising:
using a vertical lift attached to a top of a base of a patient console to provide up and down motion in a vertical axis;
using a yaw rotation device attached to the top of the vertical lift to provide a yaw rotation about the vertical axis;
using a pitch rotation device attached to the top of the yaw rotation device and configured to provide a pitch rotation about a pitch axis orthogonal to the vertical axis;
using a translation device attached to the top of the pitch rotation device and configured to provide sliding translation along a translation axis; and
using a roll rotation device attached to the translation device to roll relative to the translation device about a roll axis to provide a roll to an instrument controller assembly, wherein an angle of the translation axis and the roll axis relative to horizontal is a function of the pitch rotation provided by the pitch rotation device, wherein a direction of the translation axis and the roll axis is a function of the yaw rotation provided by the yaw rotation device.

18. The method of claim 17, further comprising using an instrument controller assembly having one or more instrument controllers connected to the roll rotation device for controlling a medical device for performing a surgical operation, and using the vertical lift, the yaw rotation device, the pitch rotation device, the translation device, and the roll rotation device provide 5-degrees of freedom to the instrument controller assembly.

19. The method of claim 18, further comprising moving the base of the patient console relative to a floor to provide an additional degree of freedom of motion.

20. The method of claim 19, further comprising positioning a medical device for a transanal procedure, a transoral procedure, or a transvaginal procedure.

* * * * *